United States Patent
Fauconet et al.

(10) Patent No.: US 7,029,556 B1
(45) Date of Patent: Apr. 18, 2006

(54) METHOD FOR PURIFYING (METH)ACRYLIC MONOMERS BY DISTILLATION

(75) Inventors: Michel Fauconet, Valmont (FR); Stephane Lepizzera, Saint Avold (FR)

(73) Assignee: Arkema, Puteaux (FR)

( * ) Notice: Subject to any disclaimer, the term of this patent is extended or adjusted under 35 U.S.C. 154(b) by 42 days.

(21) Appl. No.: 10/130,989

(22) PCT Filed: Nov. 15, 2000

(86) PCT No.: PCT/FR00/03172

§ 371 (c)(1),
(2), (4) Date: Sep. 30, 2002

(87) PCT Pub. No.: WO01/38285

PCT Pub. Date: May 31, 2001

(30) Foreign Application Priority Data

Nov. 24, 1999 (FR) .................................... 99 14777

(51) Int. Cl.
*B01D 3/34* (2006.01)
*C07C 51/44* (2006.01)
*C07C 69/54* (2006.01)

(52) U.S. Cl. .................. 203/8; 203/1; 203/49; 203/91; 562/600

(58) Field of Classification Search .............. 203/1, 203/8, 49, 91; 562/600; 526/319
See application file for complete search history.

(56) References Cited

U.S. PATENT DOCUMENTS 3,964,978 A * 6/1976 Watson ........................... 203/9
4,338,162 A * 7/1982 Johnson ......................... 203/8

FOREIGN PATENT DOCUMENTS

| FR | 1 087 186 A | | 2/1955 |
|----|----|----|----|
| FR | 2 056 825 A | | 5/1971 |
| GB | 992548 | * | 5/1965 |
| JP | 50-101313 | | 8/1975 |
| JP | 63027457 A | | 2/1988 |
| JP | 02-248402 | | 10/1990 |
| WO | WO 96/06066 | | 2/1996 |
| WO | 96/16921 | * | 6/1996 |

OTHER PUBLICATIONS

Translation of DE 197 20 767 A1.*
Patent Abstract of Japan, Publication No. 02-248402, Date of Publication Oct. 4, 1990, Application No. 01-069884, filed Mar. 22, 1989—"Agent And Method For Inhibiting Polymerization Of Acrylic Ester", Aoki Tadamichi et al.
Reference 1—Japanese patent laid-open No. 50-101313 (published Aug. 11, 1975), Application No. 49-7062 (filed Jan. 16, 1974), NIPPON SHOKUBAI Industrial Co., Ltd., Process For Preventing Polymerization Of Acrylic Acid Or Methacrylate.

* cited by examiner

*Primary Examiner*—Virginia Manoharan
(74) *Attorney, Agent, or Firm*—Millen, White, Zelano & Branigan, P.C.

(57) ABSTRACT

The invention concerns a method of purifying a (meth) acrylic monomer selected among (meth) acrylic acids and their esters, by distillation in the presence of at least a polymerisation inhibitor requiring input of oxygen and/or an inhibitor having better efficacy in the presence of oxygen for stabilizing the liquid phase. The invention is characterized in that the distillation is performed in the presence of a $NO_2$ gas, with an oxygen/organic vapor (p/p) ratio ranging between 0.02 and 3%, and with a $NO_2$ condensed organic vapor (p/p) ratio ranging between 0.01 and 50 ppm.

17 Claims, 1 Drawing Sheet

METHOD FOR PURIFYING (METH)ACRYLIC MONOMERS BY DISTILLATION

The present invention relates to a process for purifying (meth)acrylic monomers, such as acrylic acid, by distillation.

It is well known that one of the delicate points in the purification of these monomers, in particular of acrylic acid, results from the fact that these monomers polymerize easily when they are distilled.

The formation of insoluble polymers in industrial distillation equipment then causes clogging which requires stopping the plant and cleaning it.

To overcome these disadvantages, various types of stabilizing molecule are used. However, these stabilizers are most often molecules whose boiling point is markedly higher than that of the monomer. Consequently, the monomer vapors are not stabilized and the condensation thereof causes the presence of hot, liquid and nonstabilized droplets of monomer. In most cases, these droplets rapidly come into contact with a stream containing stabilizers. However, in industrial practice, the temporary or lasting existence of sites not wetted by stabilized liquid is unavoidable, and these condensation sites constitute sites of initiation and propagation of polymerization in distillation columns.

One of the solutions for avoiding the polymerization of these nonstabilized condensates consists in injecting a gas having polymerization inhibiting properties and allowing homogeneous distribution in the column. NO gas has such properties. Indeed, this molecule is a stable radical which can stop the growth of macromolecular chains and possesses a sufficiently high vapor pressure to ensure homogeneous distribution thereof in the medium. However, this molecule reacts very rapidly with oxygen to form $NO_2$, a molecule described in the literature as being capable of initiating polymerizations.

FR-A-1 567 710 describes the use of NO gas, in the absence of oxygen, during the synthesis of (meth)acrylic derivatives. FR-A-2 056 825 describes the use of NO gas, in the absence of oxygen, and of phenothiazine (inhibitor in liquid phase) during the distillation of acrylic acid. EP-A-301 879 describes the use of an inhibitor in liquid phase (phenolic compound/Mn or Ce salt pair) and of an inhibitor in gaseous phase which is either NO, or the ammonium salt of N-phenyl-N-nitrosohydroxylamine, during the distillation of monomers including acrylic acid. These documents-patents show that the use of $NO_2$ gas was not envisaged because this molecular was accepted as being capable of initiating polymerizations.

There may also be mentioned U.S. Pat. No. 4,338,162 which describes the use of nitrogen oxides, preferably nitrogen monoxide in the absence of oxygen, during the distillation of cyanoacrylic esters.

It is also possible to use molecules which generate NO in situ (for example N-phenyl-N-nitrosohydroxylamine, N,N-dinitrosophenylenediamine, and the like) for the stabilization of acrylic monomers (cf. EP-A-0 522 709 which describes the use of N',N'-dinitrosophenylenediamine as a molecule which generates NO and which recommends adding oxygen if the work is carried out in the presence of hydroquinone; WO-A-97/12851 which describes the use of the N-nitrosophenylhydroxylamine and copper salt pair to inhibit the polymerization of vinyl compounds: U.S. Pat. No. 2,741,583 which describes the use of a mixture of nitrogen oxides obtained from attacking a nitrite with an inorganic acid to stabilize acrylic esters).

Knowing that the stabilizers commonly used during the purification of acrylic acid require oxygen to be active (phenolic compounds such as hydroquinone and its methyl ether, quinone compounds such as benzoquinone) or exhibit better efficacy in the presence of oxygen (derivatives of phenothiazine, of aromatic amines, of thiocarbamates, of transition metal salts and of stable free radicals), the use of NO gas hence does not appear possible under current operating conditions.

The applicant company has therefore sought to solve this stabilization problem, while maintaining a conventional stabilization of the liquid phase in particular by the use of inhibitors requiring an introduction of oxygen.

To this effect, and in order to verify the effect reported in the literature of $NO_2$ on acrylic monomers, the applicant company has carried out trials of distillation of acrylic monomers in the presence of $NO_2$, which led it to observe that, surprisingly, under certain operating conditions, $NO_2$ gas, which is industrially of interest because it is less expensive than NO gas, provides stabilization during the distillation of the acrylic monomer, in other words plays the role of inhibitor of the gaseous phase, whereas it is generally known as a polymerization initiator.

The above conditions consist in observing on the one hand, a certain oxygen/organic vapor ratio—controlling this parameter making it possible to optimize the stability of the liquid phase—, and, on the other hand, a certain $NO_2$/organic vapor ratio—controlling this parameter making it possible to provide an inhibitory efficacy of $NO_2$ in gaseous phase and to prevent the initiation of polymerization.

The direct injection of $NO_2$ makes it possible to improve the stability of the monomers during their distillation, because of the possibility of introducing $NO_2$ directly at the critical sites not accessible to liquid (swan neck, of column, top of column, and the like), which does not allow the use of molecules generating $NO_2$ in situ.

Moreover, this direct injection offers additional advantages of the greater ease of injection of a gas compared with a liquid into an industrial distillation column and of the improvement of industrial hygiene by the infection of a gas rather than a liquid.

The subject of the present invention is therefore a process for purifying a (meth)acrylic monomer chosen from (meth) acrylic acid and esters thereof, by distillation in the presence of at least one polymerization inhibitor requiring an introduction of oxygen and/or an inhibitor requiring an introduction of oxygen and/or an inhibitor exhibiting better efficacy in the presence of oxygen far the stabilization of the liquid phase, characterized in that the distillation is also carried out in the presence of $NO_2$ gas, with an oxygen/organic vapor ratio (w/w) of between 0.0002 and 0.03, in particular of between 0.0004 and 0.005, and with an $NO_2$/organic vapor ration (w/w) of between $0.01\times10^{-6}$ and $50\times10^{-6}$, in particular of between $1\times10^{-6}$ and $30\times10^{-6}$.

In accordance with various other particular characteristics of the invention:
    the distillation is carried out in a column at a pressure of $1.33\times10^3$–$6.66\times10^5$ Pa=(10 to 500 mmg), with a temperature of 60 to 200° C. in the boiler and of 40 to 100° C. at the top or the column, the stream of monomer to be purified being continuously fed;
    oxygen is introduced into the boiler;
    gaseous $NO_2$ is introduced into the supply and/or into the sites of the column not accessible to liquid; $NO_2$ gas may be obtained from the oxidation of NO, it being possible for NO to be obtained by decomposition of reagents, as is well known to persons skilled in the art;

a (meth)acrylic monomer chosen from acrylic acid, methacrylic acid, $C_1$–$C_{10}$ alkyl acrylates and $C_1$–$C_{10}$ alkyl methacrylates, more particularly acrylic acid, is purified;

there is used, as polylmerization inhibitor requiring the introduction of oxygen, a phenolic inhibitor such as hydroquinone, methyl ether of hydroquinone, butylated hydroxytoluene or 2,4-dimethyl-6-butylphenol, and/or an inhibitor exhibiting better efficacy in the presence of oxygen, such as phenothiazine and derivatives thereof, paraphenylenediamine and derivatives thereof, a metal thiocarbamate, such as copper dibutyldithiocarbamate, a transition metal carboxylate, such as manganese acetate, a stable nitroxide radical such as N-oxyl-4-hydroxytetramethylpiperidine; and the polymerization inhibitor is introduced in an amount of 50 to 2000 ppm relative to the condensed organic vapors at the top of the column.

The following examples illustrate the present invention without, however, limiting the scope thereof.

BRIEF DESCRIPTION OF DRAWING

The attached drawing is a schematic flow sheet of the following general procedure used in the examples where the Figures as set forth in blocks correspond to the flow rates in the system in grams per hour. The detailed explanation is provided in the following description of the general procedure used in the examples.

EXAMPLES 1 to 5

General Procedure

Figure 1:
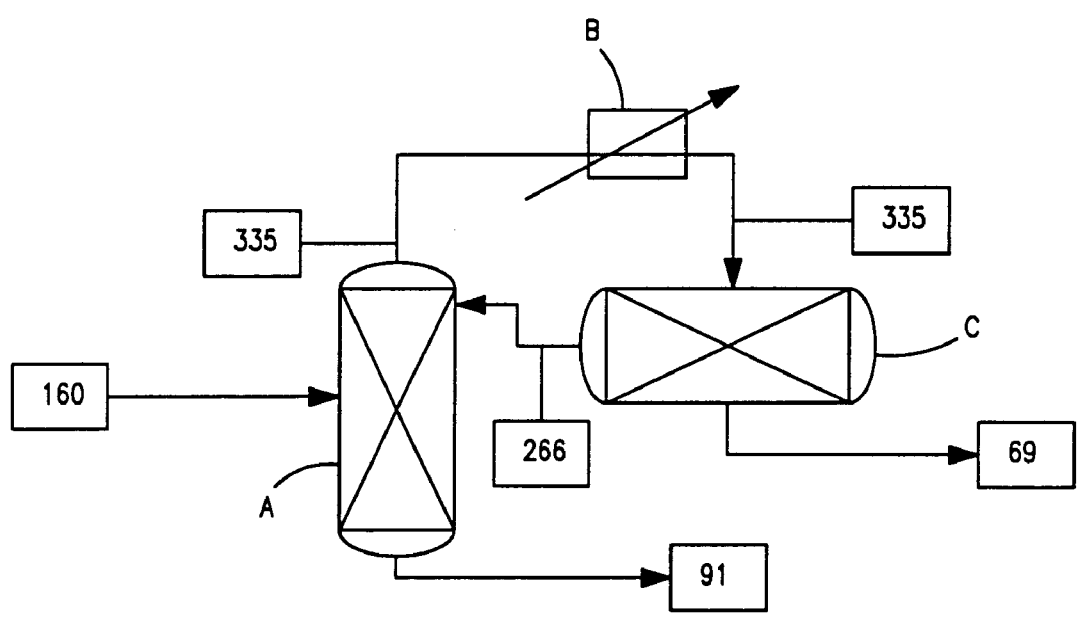

The examples presented were carried out using a glass assembly simulating a continuous distillation of one of the purification stages of acrylic acid.

This assembly consists of a distillation column equipped with perforated plates with overflow and a thermosiphon boiler, and surmounted with a swan neck.

The organic vapors are condensed using a conventional condensor. Part of the condensed liquid is recycled at the top of the column after adding liquid phase stabilizers. The distillation is carried out at a reduced pressure of $2.66 \times 10^{-1}$ Pa (200 mmHg) with a temperature of 97° C. in the boiler and 87° C. at the top of the column.

The distillation is carried out for 24 hours. The polymers appear mainly in the two areas for condensation of organic vapors: the stainless steel temperature probe at the top of the column and the connector flange of the swan neck of the condensor. At the end of the trial, these polymers are dried, and then weighed.

The stream used for all the trials presented consists of crude acrylic acid whose major impurity is acetic acid in an amount of 4% by weight. Referring to the attached drawing, this stream continuously supplies the distillation column (A) with a flow rate of 160 g/h. 69 g/h of distillate, after being condensed in condenser (B) and removed from collector (C) are collected from the top of the column and 91 g/h are drawn off at the bottom. The flow rate of organic vapor in the column is 336 g/h. 266 g/h are refluxed to the column.

The condensed organic vapors (335 g/h) are stabilized with an acrylic acid solution containing 2% by weight of hydroquinone and 0.25% of copper dibutylthiocarbamate in an amount of 2.4 g/h. A fraction of these condensed organic vapors (266 g/h) is sent back to the top of the distillation column.

Example 1

Oxygen is introduced into the boiler at the rate of 0.21 l/h, that is an oxygen/organic vapor ratio (w/w) of 0.09% (0.0009). The gaseous $NO_2$ is introduced into the supply with a flow rate of 1.9 ml/h, which corresponds to an $NO_2$ to organic vapor ratio (w/w) of 12 ppm ($12 \times 10^{-6}$).

Under these conditions, the distillate is clear, limpid, and no polymer is obtained in the two condensation areas in the column.

Example 2

This example was carried out under the same conditions as example 1, but with a gaseous $NO_2$ flow rate of 0.8 ml/h. The $NO_2$ to organic vapor ratio (w/w) is therefore 5 ppm ($5 \times 10^{-6}$).

Under these conditions, the distillate is clear, limpid, and the total quantity of polymer formed in the two condensation areas in the column is 0.5 g.

Example 3

This example was carried out under the same conditions as example 1, but with a gaseous $NO_2$ flow rate of 3.9 ml/h. The $NO_2$ to organic vapor ratio (w/w) is therefore 24 ppm ($24 \times 10^{-6}$).

Under these conditions, the distillate is clear, limpid, and the total quantity of polymer formed in the two condensation areas in the column is 3.2 g.

Example 4 (Comparative)

This example was carried out under the same conditions as example 1, but without introducing $NO_2$.

Under these conditions, the distillate is clear, limpid, and the total quantity of polymer formed in the two condensation areas in the column is 8.1 g.

Example 5 (Comparative)

This example was carried out under the same conditions as example 1, but with a gaseous $NO_2$ flow rate of 10.1 ml/h. The $NO_2$ to organic vapor ratio (w/w) is therefore 62 ppm ($62 \times 10^{-6}$).

Under these conditions, the presence of polymers is observed in the distil late (substantial cloudiness) and the total quantity of polymer formed in the two condensation areas in the column is 1.1 g.

The invention claimed is:

1. A process for purifying a (meth)acrylic monomer selected from the group consisting of (meth)acrylic acids and esters thereof, comprising conducting distillation in the presence of at least one polymerization inhibitor requiring an introduction of oxygen and/or an inhibitor exhibiting better efficacy in the presence of oxygen for the stabilization of resultant liquid phase, the improvement comprising conducting the distillation in a distillation column in the presence of introduced gaseous $NO_2$, with an oxygen/organic vapor ratio (w/w) of between 0.0002 and 0.03, and with an $NO_2$/organic vapor ratio (w/w) of between $0.01 \times 10^{-6}$ and $50 \times 10^{-6}$.

2. The process as claimed in claim 1, wherein the distillation is carried out with an oxygen/organic vapor ratio (w/w) of between 0.0004 and 0.005.

3. The process as claimed in claim 2, wherein the distillation is carried out with an $NO_2$/organic vapor ratio (w/w) of between $1 \times 10^{-6}$ and $30 \times 10^{-6}$.

4. The process as claimed in claim 1, wherein the distillation is carried out with an $NO_2$/organic vapor ratio (w/w) of between $1 \times 10^{-6}$ and $30 \times 10^{-6}$.

5. The process as claimed in claim 1, wherein the distillation is carried out in a column at a pressure of $1.33 \times 10^3$ to $6.66 \times 10^5$ Pa (10 to 500 mmHg), with a boiler temperature of 60–200° C. and a temperature of 40–100° C. at the top of the column, the monomer to be purified being continuously introduced as a feed stream to the column.

6. The process as claimed in claim 5, wherein oxygen is introduced into the boiler.

7. The process as claimed in claim 6, wherein gaseous $NO_2$ is introduced into the feed stream and/or into sites in the column not accessible to liquid.

8. The process as claimed in claim 4, wherein gaseous $NO_2$ is introduced into the feed stream and/or into sites in the column not accessible to liquid.

9. The process as claimed in claim 5, wherein the distillation is carried out with an oxygen/organic vapor ratio (w/w) of between 0.0004 and 0.005.

10. The process as claimed in claim 9, wherein the distillation is carried out with an $NO_2$/organic vapor ratio (w/w) of between $1 \times 10^{-6}$ and $30 \times 10^{-6}$.

11. The process claimed in claim 10, wherein the $NO_2$ is introduced into at least one site in the distillation column not accessible to liquid.

12. The process as claimed in claim 5, wherein the distillation is carried out with an $NO_2$/organic vapor ratio (w/w) of between $1 \times 10^{-6}$ and $30 \times 10^{-6}$.

13. The process as claimed in claim 1, wherein the (meth) acrylic monomer is selected from the group consisting of acrylic acid, methacrylic acid, $C_1$–$C_{10}$ alkyl acrylates and $C_1$–$C_{10}$ alkyl methacrylates.

14. The process as claimed in claim 1, wherein the at least one polymerization inhibitor requires the introduction of oxygen, and is selected from the group consisting of a phenolic inhibitor hydroquinone, methyl ether of hydroquinone, butylated hydroxytoluene and 2,4-dimethyl-6-butylphenol.

15. The process as claimed in claim 1, wherein organic vapors are condensed at the top of the column and the at least one polymerization inhibitor is introduced in an amount of 50 to 2000 ppm relative to the condensed organic vapors at the top of the column.

16. The process as claimed in claim 1, wherein the at least one polymerization inhibitor exhibits better efficacy in the presence of oxygen, and is selected from the group consisting of phenothiazine and derivatives thereof, paraphenylenediamine and derivatives thereof, a metal thiocarbamate, a transition metal carboxylate, and a compound having a stable nitroxide radical.

17. The process claimed in claim 1, wherein the $NO_2$ is introduced into at least one site in the distillation column not accessible to liquid.

* * * * *

UNITED STATES PATENT AND TRADEMARK OFFICE
CERTIFICATE OF CORRECTION

| | | |
|---|---|---|
| PATENT NO. | : 7,029,556 B1 | Page 1 of 1 |
| APPLICATION NO. | : 10/130989 | |
| DATED | : April 18, 2006 | |
| INVENTOR(S) | : Fauconet et al. | |

It is certified that error appears in the above-identified patent and that said Letters Patent is hereby corrected as shown below:

Column 5, line 15 reads "claimed in claim 4," should read -- claimed in claim 5, --

Signed and Sealed this

Thirtieth Day of January, 2007

JON W. DUDAS
*Director of the United States Patent and Trademark Office*